US010822590B2

(12) United States Patent
Shin et al.

(10) Patent No.: US 10,822,590 B2
(45) Date of Patent: *Nov. 3, 2020

(54) BACTERIOPHAGE AND COMPOSITION COMPRISING SAME

(71) Applicant: CJ CHEILJEDANG CORPORATION, Seoul (KR)

(72) Inventors: Eun Mi Shin, Seoul (KR); Gi Duk Bae, Seoul (KR); Jae Won Kim, Yongin-si (KR)

(73) Assignee: CJ CHEILJEDANG CORPORATION, Seoul (KR)

(*) Notice: Subject to any disclaimer, the term of this patent is extended or adjusted under 35 U.S.C. 154(b) by 70 days.

This patent is subject to a terminal disclaimer.

(21) Appl. No.: 16/250,713

(22) Filed: Jan. 17, 2019

(65) Prior Publication Data

US 2019/0153399 A1 May 23, 2019

Related U.S. Application Data

(62) Division of application No. 15/304,402, filed as application No. PCT/KR2015/003705 on Apr. 14, 2015, now Pat. No. 10,240,129.

(30) Foreign Application Priority Data

Apr. 15, 2014 (KR) .................. 10-2014-0044997

(51) Int. Cl.
| | | |
|---|---|---|
| *C12N 7/00* | (2006.01) | |
| *A23K 10/18* | (2016.01) | |
| *A23K 20/195* | (2016.01) | |
| *A23K 50/70* | (2016.01) | |
| *A23K 50/75* | (2016.01) | |
| *A61K 35/76* | (2015.01) | |
| *A23K 20/153* | (2016.01) | |

(52) U.S. Cl.
CPC ............... *C12N 7/00* (2013.01); *A23K 10/18* (2016.05); *A23K 20/153* (2016.05); *A23K 20/195* (2016.05); *A23K 50/70* (2016.05); *A23K 50/75* (2016.05); *A61K 35/76* (2013.01); *C12N 2795/00021* (2013.01); *C12N 2795/00032* (2013.01); *C12N 2795/10121* (2013.01); *C12N 2795/10132* (2013.01)

(58) Field of Classification Search
CPC ............ C12N 7/00; C12N 2795/10132; C12N 2795/10121; C12N 2795/00021; C12N 2795/00032; A61K 35/76; A23K 50/70; A23K 50/75; A23K 20/153; A23K 10/18; A23K 20/195; A61P 31/04

See application file for complete search history.

(56) References Cited

U.S. PATENT DOCUMENTS 8,309,077 B2 * 11/2012 Murthy .................. A23K 50/80
424/93.6
9,938,506 B2 4/2018 Seo et al.

FOREIGN PATENT DOCUMENTS

| JP | 2011-509653 A | 3/2011 |
| KR | 10-2012-0111535 A | 10/2012 |
| KR | 10-1299179 B1 | 8/2013 |
| KR | 10-1381793 B1 | 4/2014 |

OTHER PUBLICATIONS

Li et al., "Complete Genome Sequence of the Novel Lytic Avian Pathogenic Coliphage NJ01", Journal of Virology, vol. 86, No. 24—2 pages (Dec. 2012).
Office Action of corresponding Chinese Patent Application No. 201580032048.3—6 pages (dated Jan. 22, 2019).
Extended European Search Report of corresponding European Patent Application No. 15779395.1—9 pages (dated Aug. 3, 2017).
Huff et al., "Method of administration affects the ability of bacteriophage to prevent colibacillosis in 1-day-old broiler chickens", Poultry Science, vol. 92, No. 4—5 pages (Apr. 2013).
Lau et al., "Efficacy of a bacteriophage isolated from chickens as a therapeutic agent for colibacillosis in broiler chickens", Poultry Science, vol. 89, No. 12—8 pages (Dec. 2010).
Oliveira et al., "In vivo efficiency evaluation of a phage cocktail in controlling severe colibacillosis in confined conditions and experimental poultry houses", Veterinary Microbiology, vol. 146, No. 3-4—6 pages (Dec. 2010).
Tsonos et al., "A cocktail of in vitro efficient phages is not a guarantee for in vivo therapeutic results against avian colibacillosis", Veterinary Microbiology, vol. 171, No. 3-4—10 pages (Jul. 2014).
International Search Report of Patent Application No. PCT/KR2015/003705 and its English Translation—4 pages (dated Jul. 15, 2015).

* cited by examiner

*Primary Examiner* — Kade Ariani
(74) *Attorney, Agent, or Firm* — Knobbe Martens Olson & Bear LLP (57) ABSTRACT

The present invention relates to a novel bacteriophage ΦCJ25 (KCCM11463P) and a composition comprising the same as an active ingredient. In addition, the present invention relates to a method for preventing and/or treating infectious diseases caused by avian pathogenic *Escherichia coli* (APEC) of birds by using the bacteriophage ΦCJ25 (KCCM11463P) or the composition.

9 Claims, 3 Drawing Sheets

BACTERIOPHAGE AND COMPOSITION COMPRISING SAME

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present invention relates to a novel bacteriophage having a specific ability to kill avian pathogenic *Escherichia coli* (APEC), a composition including the same, and a method for preventing or treating infectious diseases of birds using the novel bacteriophage or the composition.

BACKGROUND ART

*Escherichia coli* (hereinafter also referred to as *E. coli*) is a Gram-negative, short rod bacterium of genus *Escherichia*, family Enterobacteriaceae, and one of normal flora found in intestines of various animals including mammals. Most strains of *Escherichia coli* are non-pathogenic and can cause opportunistic infection, but some highly pathogenic strains cause various intestinal diseases and sepsis in animals including humans.

Among these strains of *Escherichia coli*, avian pathogenic *E. coli* causes infection through the respiratory tract of birds such as chickens, geese, turkeys, and the like, and is known to pass into the avian body through the respiratory mucous membrane. Avian pathogenic *E. coli* causes diseases mostly in poultry with respect to respiratory diseases in birds, which leads to enormous economic damage in the poultry industry.

Meanwhile, a bacteriophage refers to a bacterium specific virus that prevents and inhibits growth of a bacterium infected with a specific bacteriophage. As bacteriophages have stronger host specificity than antibiotics, and recent emergence of bacteria resistant to antibiotics and residual antibiotics in animals are growing problems, application of bacteriophages has drawn great interest.

Studies on bacteriophages have been actively performed in many countries, and there has been an increasing tendency to obtain approval from the Food and Drug Administration (FDA) for compositions using bacteriophages in addition to patent applications for bacteriophages.

However, bacteriophage related technologies for prevention and/or treatment of infectious diseases, which are important issues in the aviculture industry including poultry farming, due to avian pathogenic *Escherichia coli* are still insufficient, and therefore, there is a need for such bacteriophages and development of relevant technologies.

DISCLOSURE

Technical Problem

As a result of earnest investigation aimed at overcoming the emergence of bacteria resistant to antibiotics and residual antibiotics in animals and at effectively preventing and treating infectious diseases of birds, the present inventors isolated a novel bacteriophage ΦCJ25 (KCCM11463P) having a specific ability to kill avian pathogenic *Escherichia coli* causing respiratory diseases of poultry from natural sources.

In addition, the present inventors identified morphological, biochemical, and genetic properties of the novel bacteriophage, confirmed that the bacteriophage has excellent acid resistance, heat resistance, and drying resistance, and developed antibiotics, disinfectants, additives for feeds, and other compositions using the bacteriophage, a composition for preventing or treating infectious diseases in birds, and a method for preventing or treating diseases using the same.

It is an object of the present invention to provide a novel bacteriophage ΦCJ25 (KCCM11463P) having a specific ability to kill avian pathogenic *Escherichia coli*.

It is another object of the present invention to provide a composition for preventing and/or treating infectious diseases caused by avian pathogenic *Escherichia coli*, including the bacteriophage ΦCJ25 (KCCM11463P) as an active ingredient.

It is a further object of the present invention to provide antibiotics, additives for feeds, additives for drinking water, feeds, drinking water, disinfectants or detergents, including the bacteriophage ΦCJ25 (KCCM11463P) as an active ingredient.

It is yet another object of the present invention to provide a method for preventing and/or treating infectious diseases caused by avian pathogenic *Escherichia coli* using the bacteriophage ΦCJ25 (KCCM11463P) or the composition including the bacteriophage ΦCJ25 (KCCM11463P) as an active ingredient.

Technical Solution

One aspect of the present invention provides a novel bacteriophage ΦCJ25 (KCCM11463P) having a specific ability to kill avian pathogenic *Escherichia coli*.

Another aspect of the present invention provides a composition for preventing or treating infectious diseases caused by avian pathogenic *Escherichia coli*, including the bacteriophage ΦCJ25 (KCCM11463P) as an active ingredient.

A further aspect of the present invention provides antibiotics, additives for feeds, additives for drinking water, feeds, drinking water, disinfectants or detergents, including the bacteriophage ΦCJ25 (KCCM11463P) as an active ingredient.

Yet another aspect of the present invention provides a method for preventing or treating infectious diseases caused by avian pathogenic *Escherichia coli*, including: administering the bacteriophage ΦCJ25 (KCCM11463P) or the composition including the bacteriophage ΦCJ25 (KCCM11463P) as an active ingredient to birds.

Advantageous Effects

The bacteriophage ΦCJ25 (KCCM11463P) according to the present invention has an effect of having a specific ability to kill avian pathogenic *Escherichia coli*.

Further, the bacteriophage ΦCJ25 (KCCM11463P) according to the present invention has excellent acid resistance, heat resistance, and drying resistance, and thus can be employed not only as an agent for preventing or treating infectious diseases caused by avian pathogenic *Escherichia coli* at various ranges of temperature, pH, and dry conditions but also as antibiotics, additives for feeds, additives for drinking water, feeds, drinking water, disinfectants, detergents, and the like, including the bacteriophage ΦCJ25 (KCCM11463P) as an active component.

Further, the present invention provides the bacteriophage ΦCJ25 (KCCM11463P) or antibiotics including the same as an active ingredient, and the antibiotics have effects in that the antibiotics have specificity for avian pathogenic *Escherichia coli* as compared to prior antibiotics and thus selectively kill specific pathogenic bacteria without killing beneficial bacteria; and that the antibiotics do not induce drug resistance, resulting in extension of lifetime of products as compared to prior antibiotics.

Further, the present invention has effects of preventing or treating infectious diseases caused by avian pathogenic *Escherichia coli* by administering the bacteriophage ΦCJ25 (KCCM11463P) or the composition including the bacteriophage ΦCJ25 (KCCM11463P) as an active ingredient to birds.

EMBODIMENTS

Hereinafter, embodiments of the present invention will be described in more detail. Description of details apparent to a person having ordinary knowledge in the art will be omitted herein.

One embodiment of the present invention provides a novel bacteriophage ΦCJ25 (KCCM11463P) (hereinafter referred to as 'ΦCJ25') having a specific ability to kill avian pathogenic *Escherichia coli* (APEC).

Avian pathogenic *Escherichia coli* refers to *Escherichia coli* that is transmitted through the respiratory tract of birds such as chickens, geese, turkeys, and the like, and that can cause infectious diseases of birds, specifically avian colibacillosis. Specifically, avian pathogenic *Escherichia coli* penetrates into the body of birds through the mucous membrane of the respiratory tract, and causes various diseases such as sepsis, granuloma, air sacculitis, salpingitis, arthritis, and the like. Avian pathogenic *Escherichia coli* is a Gram-negative bacillus just like general *Escherichia coli*, has peritrichous flagella for motility, and is an aerobic or facultative anaerobic bacterium which decomposes lactose and fructose to generate acids and gases.

Avian pathogenic *Escherichia coli* grows well on common media and is capable of growing at a temperature of about 7° C. to about 48° C. with ideal growth temperature ranging from about 35° C. to about 37° C. Specifically, at around 42° C. which is close to body temperature of birds, expression of pathogenic factors is effectively performed. Further, avian pathogenic *Escherichia coli* can grow at pH ranging from pH 4.5 to pH 9.0.

A bacteriophage is a bacteria-specific virus capable of infecting a specific bacterium and inhibiting growth of the bacterium, and is a virus including single or double-stranded deoxyribonucleic acid (DNA) or ribonucleic acid (RNA) as a genetic material.

Figure 1:
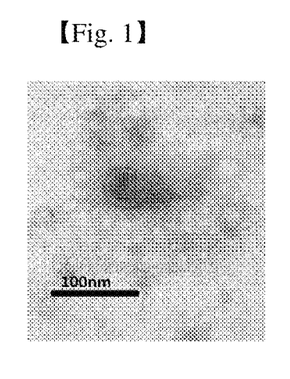
FIG. 1 is an electron microscope image of a novel bacteriophage ΦCJ25 (KCCM11463P) (hereinafter referred to as 'ΦCJ25').
Figure 5:
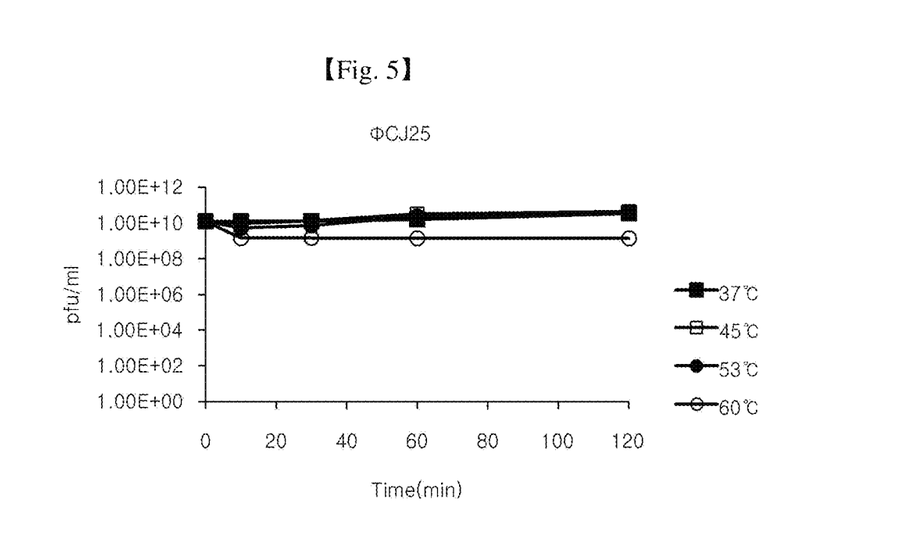
FIG. 5 is a graph depicting results of heat resistance experiment of a novel bacteriophage ΦCJ25.
Figure 6:
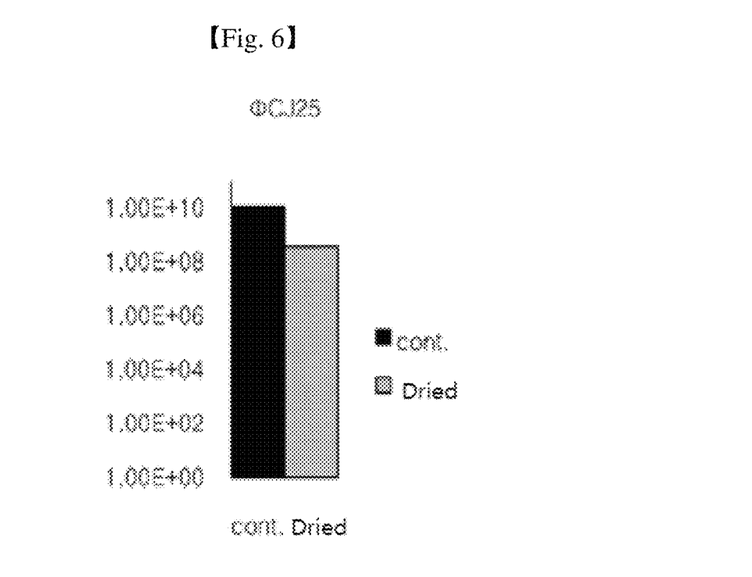
FIG. 6 is a graph depicting results of drying resistance experiment of a novel bacteriophage ΦCJ25.

Specifically, the bacteriophage ΦCJ25 according to the embodiment of the present invention is a bacteriophage that has species specificity of selectively infecting avian pathogenic *Escherichia coli* and morphologically belongs to Myoviridae having an icosahedral capsid and a contractile tail (see FIG. 1). Homology between a nucleotide sequence of the bacteriophage ΦCJ25 and decoded nucleotide sequences of other bacteriophages is compared and results are shown in Table 1. The bacteriophage ΦCJ25 shows stable acid resistance at pH 3.5 to pH 11.0 without losing activity (FIG. 4), and in terms of heat resistance, the bacteriophage ΦCJ25 does not show activity decline even when exposed to 50° C. or more (for example, 53° C.) for two hours (FIG. 5). In terms of drying resistance, the bacteriophage ΦCJ25 shows activity decline of about 2 log after drying (FIG. 6). DNA nucleotide sequence of the bacteriophage ΦCJ25 is set forth in SEQ ID NO: 1 of Sequence List.

The bacteriophage ΦCJ25 is a novel bacteriophage isolated by the present inventor, and was deposited at the Korean Culture Center of Microorganisms (KCCM) (361-221, Hongje 1-dong, Seodaemun-gu, Seoul, Korea) on Oct. 25, 2013 under accession number KCCM 11462P.

Another embodiment of the present invention provides a composition for preventing or treating infectious diseases caused by avian pathogenic *Escherichia coli*, including the bacteriophage ΦCJ25 as an active ingredient.

Since the bacteriophage ΦCJ25 exhibits antibacterial activity capable of specifically killing avian pathogenic *Escherichia coli*, the bacteriophage ΦCJ25 can be utilized in prevention or treatment of diseases caused by infection with avian pathogenic *Escherichia coli*. Examples of infectious diseases caused by avian pathogenic *Escherichia coli* include avian colibacillosis, without being limited thereto.

Herein, the term "avian colibacillosis" refers to a disease occurring in the respiratory tract of birds due to infection with pathogenic *Escherichia coli*, and symptoms thereof include air sacculitis, perihepatitis, peritonitis, pericarditis, salpingitis, omphalitis, osteomyelitis or septicemia, thereby causing growth delay and mortality of infected birds.

Herein, the term "preventing" or "prevention" refers to all actions to inhibit the diseases or delay occurrence of the diseases by administering the bacteriophage ΦCJ25 and/or the composition including the bacteriophage ΦCJ25 as an active ingredient to an animal.

Herein, the term "treating" or "treatment" refers to all actions to improve or ameliorate symptoms of infectious diseases by administering the bacteriophage ΦCJ25 and/or the composition including the bacteriophage ΦCJ25 as an active ingredient to an animal.

The composition for preventing or treating infectious diseases caused by avian pathogenic *Escherichia coli* according to this embodiment may include the bacteriophage ΦCJ25 in amounts of $5\times10^2$ pfu/ml to $5\times10^{12}$ pfu/ml, specifically, $1\times10^6$ pfu/ml to $1\times10^{10}$ pfu/ml.

The composition for preventing or treating infectious diseases caused by avian pathogenic *Escherichia coli* according to this embodiment may further include pharmaceutically acceptable carriers, and may be formulated with the carriers to provide foods, medicines, additives for feeds or additives for drinking water, and the like.

Herein, the term "pharmaceutically acceptable carriers" refers to carriers or diluents that do not stimulate an organism and do not inhibit biological activity and properties of administered compounds.

Types of carriers applicable to this embodiment are not particularly limited and any pharmaceutically acceptable carriers commonly used in the art may be utilized. Examples of the carriers may include saline, distilled water, Ringer's solution, buffered saline, an albumin injection solution, a dextrose solution, a maltodextrin solution, glycerol, and ethanol, without being limited thereto. These may be used alone or in combination thereof.

Furthermore, as needed, other common additives such as antioxidants, buffered solutions and/or cytostatics may be added to the composition according to the present invention, and diluents, dispersants, surfactants, binders and/or lubricants may be further added to the composition according to the present invention to formulate injectable formulations such as aqueous solutions, suspensions and emulsions, pills, capsules, granules, and tablets.

Methods for administering the composition for preventing or treating infectious diseases caused by avian pathogenic *Escherichia coli* according to this embodiment are not particularly limited, and any methods commonly used in the related art may be used. One example of the administration method may include oral administration or parenteral administration.

Examples of dosage forms for oral administration may include troches, lozenges, tablets, water soluble suspensions, oil-based suspensions, formulated powder, granules, emulsions, hard capsules, soft capsules, syrups, and elixirs. In order to formulate the composition according to this embodiment into dosage forms such as tablets or capsules, binders such as lactose, saccharose, sorbitol, mannitol, starches, amylopectin, cellulose and gelatin; excipients such as dicalcium phosphate; disintegrators such as corn starch and sweet potato starch; lubricants such as magnesium stearate, calcium stearate, sodium stearyl fumarate and polyethylene glycol wax may be further included, and for capsule formulation, liquid carriers such as fatty oils may be further included in addition to the aforementioned substances.

Methods for parenterally administering the composition of this embodiment may include, for example, intravenous injection, intraperitoneal administration, intramuscular administration, subcutaneous administration, and topical administration, and a method of applying or spraying the composition according to the present invention to an affected region, without being limited thereto.

In order to formulate parenteral dosage forms, for example, the composition of this embodiment may be formulated into dosage forms for injection such as subcutaneous injection, intravenous injection and intramuscular injection; suppositories; or dosage forms for spraying such as aerosols so as to permit inhalation through inhalers, without being limited thereto. In order to formulate dosage forms for injection, the composition of this embodiment may be mixed with stabilizers or buffering agents in water to prepare solutions or suspensions, which are formulated into dosage forms for unit administration such as ampoules or vials. When the composition is formulated into dosage forms for spraying such as aerosols, the composition may be formulated with propellants and the like together with additives such that a concentrate dispersed in water or wetted powder is dispersed therein.

Suitable amounts of applying, spraying or administering the composition for preventing or treating infectious diseases caused by avian pathogenic *Escherichia coli* according to this embodiment may differ according to factors such as age, body weight and sex of animals, degree of disease symptoms, ingested foods, rate of excretion, and the like in addition to a method for formulating the composition, an administration method, administration time and/or routes for administration, and a generally skilled veterinarian can easily determine and prescribe dose amounts effective for intended treatment.

A further embodiment of the present invention provides antibiotics including the bacteriophage ΦCJ25 as an active ingredient.

Herein, the term "antibiotics" refers to a preparation that is administered to animals including humans in medicine form and exhibits efficacy of sterilizing bacteria, and is used as a general term for antiseptics, germicides and antibacterial agents.

Antibiotics of this embodiment including the bacteriophage ΦCJ25 as an active ingredient have effects in that the antibiotics have specificity for avian pathogenic *Escherichia coli* as compared to typical antibiotics and thus kill specific pathogenic bacteria, but not beneficial bacteria; and in that the antibiotics do not induce antibiotic resistance, causing extension of lifetime of products as compared to typical antibiotics.

Yet another embodiment of the present invention provides an additive for avian feeds or avian drinking water, which includes the bacteriophage ΦCJ25 as an active ingredient.

Birds as a subject to which the additives for avian feeds or the additives for avian drinking water are applied are not particularly limited, but birds in this embodiment are particularly poultry.

Herein, poultry is a generic name for animals belonging to birds among livestock. Poultry is not particularly limited, and may comprise at least one selected from the group consisting of chickens, geese, turkeys, and the like.

The additives for avian feeds or the additives for avian drinking water may be used by separately preparing additives for feeds or additives for avian drinking water using the bacteriophage ΦCJ25 or the composition including the same and mixing feeds or drinking water with the additives, or directly adding the bacteriophage ΦCJ25 or the composition including the same in a process of preparing feeds or drinking water.

The bacteriophage ΦCJ25 or the composition including the bacteriophage ΦCJ25 as an active ingredient used in the form of additives for feeds or additives for drinking water according to this embodiment may be a liquid form or a dried form, for example, a dried powder form.

For example, the bacteriophage ΦCJ25 according to the present invention is mixed in powder form in amounts of 0.05% by weight (wt %) to 10 wt %, specifically 0.1 wt % to 2 wt %, based on the weight of additives for feeds.

Methods for drying the additives for feeds or additives for drinking water according to this embodiment to yield dried powder are not particularly limited, and any methods commonly used in the related art may be utilized. Examples of the drying method may include air drying, natural drying, spray drying, and lyophilization, without being limited thereto. These methods may be used alone or in combination thereof.

The additives for feeds or additives for drinking water according to this embodiment may further include other non-pathogenic microorganisms. The microorganisms may be selected from the group consisting of *Bacillus* sp. such as *Bacillus subtilis* capable of producing proteases, lipases and/or glycosyltransferases; lactic acid bacteria such as *Lactobacillus* sp. having physiological activity and organic material decomposing capability under anaerobic conditions like the stomach of cattle; filamentous bacteria such as *Aspergillus oryzae* having effects of weight gain in animals, increase in milk production, and increase of digestion-absorption rate of feeds; and yeasts such as *Saccharomyces*

*cerevisiae* and the like. These microorganisms may be used alone or in combination thereof.

The additives for feeds or additives for drinking water according to this embodiment including the bacteriophage ΦCJ25 as an active ingredient may further include other additives as needed. Examples of usable additives may include binders, emulsifiers, and preservatives added for prevention of quality deterioration of feeds or drinking water; amino acid, vitamin, enzyme, probiotics, flavoring agents, non-protein nitrogen compounds, silicate, buffering agents, coloring agents, extracting agents or oligosaccharides that are added in order to increase utility of feeds or drinking water; and other supplements to feeds, and the like. These additives may be used alone or in combination thereof.

The additives for feeds according to the present invention may be present in amounts of 0.05 parts by weight to 10 parts by weigh, specifically 0.1 parts by weight to 2 parts by weight, based on 100 parts by weight of feeds. The additives for drinking water according to the present invention may be present in amounts of 0.0001 parts by weight to 0.01 parts by weight, specifically 0.001 parts by weight to 0.005 parts by weight, based on 100 parts by weight of drinking water. Within these ranges, the additives allow activity of the bacteriophage ΦCJ25 against avian pathogenic *Escherichia coli* to be sufficiently displayed.

Yet another embodiment of the present invention provides feeds or drinking water prepared by adding the additives for feeds or the additives for drinking water including the bacteriophage ΦCJ25 as an active ingredient to feeds or drinking water, or directly adding the bacteriophage ΦCJ25 thereto.

Feeds used in this embodiment are not particularly limited, and any feeds commonly used in the related art may be used. Examples of the feeds may include vegetable feeds such as grains, root vegetables, food processing byproducts, algae, fibers, pharmaceutical byproducts, oils and fats, starches, residues or byproducts of grain, and the like; and animal feeds such as proteins, inorganic substances, oils and fats, minerals, single cell proteins, and animal planktons or foods. These feeds are used alone or in combination thereof.

Drinking water used in this embodiment is not particularly limited, and any drinking water commonly used in the related art may be used.

Yet another embodiment of the present invention provides disinfectants or detergents including the bacteriophage ΦCJ25 as an active ingredient. Dosage forms of the disinfectants or detergents are not particularly limited, and any dosage forms commonly used in the related art may be used.

In order to remove avian pathogenic *Escherichia coli*, the disinfectants may be sprayed to habitats of birds, slaughterhouses, dead regions, kitchens, and cooking equipment, without being limited thereto.

The detergents may be used to wash a surface of the dermis or body parts of birds that are exposed to or can be exposed to avian pathogenic *Escherichia coli*, without being limited thereto.

Yet another embodiment of the present invention provides a method for preventing or treating infectious diseases caused by avian pathogenic *Escherichia coli* using the bacteriophage ΦCJ25 or the composition including the bacteriophage ΦCJ25 as an active ingredient.

Specifically, the prevention method or treatment method of this embodiment includes administering a pharmaceutically effective amount of the bacteriophage ΦCJ25 or the composition including the bacteriophage ΦCJ25 as an active ingredient to birds that are exposed to or can be exposed to avian pathogenic *Escherichia coli*. Suitable total amounts of the bacteriophage ΦCJ25 or the composition including the same per day may be determined by a physician within proper medicinal judgment, as apparent to those skilled in the art.

A concrete pharmaceutically effective amount of the bacteriophage ΦCJ25 or the composition including the bacteriophage ΦCJ25 as an active ingredient to certain birds may be determined by taking into account the sorts and degree of reaction to achieve, age, body weight, general health condition, sex or diet of corresponding individuals, administration time and administration routes of bacteriophage ΦCJ25 or a composition including the same, and secretion rate of the composition, treatment period, and the like, and may differ depending upon various factors and similar factors well known in the field of medicine including components of medicines that are used simultaneously or at different times.

The bacteriophage ΦCJ25 or the composition including the bacteriophage ΦCJ25 as an active ingredient may be administered in the form of a pharmaceutical preparation to birds by intranasal spraying, or directly added to avian feeds or drinking water so as to be digested, and may be mixed in the form of additives for feeds or additives for drinking water with feeds or drinking water and then administered.

Routes and methods for administration of the bacteriophage ΦCJ25 or the composition including the bacteriophage ΦCJ25 as an active ingredient are not particularly limited, and the administration may be realized by any routes and methods so long as the administration allows the bacteriophage ΦCJ25 or the composition including the same to reach desired tissues. Namely, the bacteriophage ΦCJ25 or the composition including the bacteriophage ΦCJ25 as an active ingredient may be administered by various oral or parenteral routes, and examples of administration may include oral, rectal, topical, intravenous, intraperitoneal, intramuscular, intra-arterial, trans-dermal, intranasal, inhalation, and the like, without being limited thereto.

Hereinafter, the present invention will be described in more detail with reference to a preferred example. It should be understood that these examples are not to be construed in any way as limiting the present invention.

EXAMPLE 1

Isolation of Bacteriophage that Infects Avian Pathogenic *Escherichia coli*

<Example 1-1>

Bacteriophage Screening and Single Bacteriophage Isolation 50 ml of a specimen obtained from chicken feces collected around Samwhawonjong farm in Gwangcheon, Hongsung-gun, Chungcheong Province was centrifuged at 4,000 rpm for 10 minutes, and the resulting supernatant was filtered through a 0.45 λm filter to prepare a specimen liquid, which in turn was used to perform a soft agar overlay method. The soft agar overlay method refers to a method of observing bacteriophage lysis using a host cell growing on top-agar (attached to a solid medium using 0.7% agar).

Specifically, 150 μl of a shaking culture solution ($OD_{600}=2$) of avian pathogenic *Escherichia coli* (E09-19) obtained from the Department of Veterinary Medicine of Konkuk University and 2 ml of 10×LB medium (10 g/l of tryptophan; 5 g/l of yeast extract; 10 g/l of NaCl) were mixed with 18 ml of the filtered specimen liquid, followed by culturing at 30° C. for 18 hours, and the resulting cultured solution was centrifuged at 4,000 rpm for 10 minutes, and the resulting supernatant was filtered through a 0.45 μm filter. Subsequently, a mixed solution consisting of 3 ml of 0.7% (w/v) agar and 150 μl of a shaking culture solution ($OD_{600}$=2) of avian pathogenic *Escherichia coli* (E09-19) was poured and solidified on an LB medium plate, to which 10 μl of the specimen liquid was added dropwise, followed by culturing at 30° C. for 18 hours, thereby identifying formation of plaques.

Since it is known that one sort of bacteriophage is present per plaque, the inventors tried to isolate single bacteriophages from the formed plaques. Specifically, 400 μl of SM solution (5.8 g/l of NaCl; 2 g/l of $MgSO_4 7H_2O$; 50 ml of 1M Tris-HCl (pH 7.5)) was added to the plaques and left at room temperature for 4 hours, thereby obtaining a bacteriophage solution.

Subsequently, 100 μl of the bacteriophage solution was mixed with 12 ml of 0.7% (w/v) agar and 500 μl of a shaking culture solution ($OD_{600}$=2) of avian pathogenic *Escherichia coli* (E09-19), which was used to perform a soft agar overlay method using an LB medium plate having a diameter of 150 mm wherein cultivation was performed until the bacteriophage was completely lysed. After completion of cultivation, 15 ml of SM solution was added to the LB medium plate and left at room temperature for 4 hours, thereby obtaining a bacteriophage solution.

To the obtained solution, 1% (v/v) chloroform was added and mixed for 10 minutes, followed by centrifugation at 4,000 rpm for 10 minutes, thereby obtaining a supernatant, which in turn was filtered through a 0.45 μm filter, thereby obtaining a final specimen.

<Example 1-2>

Large Scale Culture and Purification of Bacteriophage

Bacteriophage obtained in Example 1-1 was cultured at large scale using avian pathogenic *Escherichia coli* (E09-19), and then the bacteriophage was purified therefrom.

Specifically, avian pathogenic *Escherichia coli* (E09-19) was shaking cultured, and inoculated at $1.5 \times 10^{10}$ cfu, followed by centrifuging at 4,000 rpm for 10 minutes, and re-suspending in 4 ml of SM solution. To this, the bacteriophage was added at $1.5 \times 10^6$ pfu with multiplicity of infection (MOI) of 0.0001, and then left at room temperature for 20 minutes.

Next, 150 ml of LB medium was inoculated therewith, and cultured at 30° C. for 6 hours. After completion of cultivation, chloroform was added to a volume of 1% (v/v) of the final volume, followed by stirring for 20 minutes, to which DNase I and RNase A as restriction enzymes were added in a final concentration of 1 μg/ml, respectively, and left at 30° C. for 30 minutes. Subsequently, sodium chloride and polyethylene glycol were added to a final concentration of 1M and 10% (w/v), respectively, and left at 4° C. for 3 hours, followed by centrifuging at 4° C. and 12,000 rpm for 20 minutes, thereby obtaining a precipitate.

The obtained precipitate was suspended in 5 ml of SM solution and then left at room temperature for 20 minutes, 4 ml of chloroform was added thereto with stirring, followed by centrifugation at 4° C. with 4,000 rpm for 20 minutes, thereby obtaining a supernatant. The supernatant was filtered through a 0.45 μm filter, followed by ultracentrifugation (35,000 rpm, 1 hour, 4° C.) using a glycerol density gradient method (density: 40%, 5% glycerol), thereby purifying a bacteriophage.

The present inventors isolated a bacteriophage having a specific ability to kill avian pathogenic *Escherichia coli* from samples collected from chicken feces on farms, which was designated as "Bacteriophage ΦCJ25" and deposited at the Korean Culture Center of Microorganisms (KCCM) (361-221 Hongje 1-dong, Seodaemun-gu, Seoul, Korea) on Oct. 25, 2013 under accession number KCCM 11462P.

<Example 2>

Morphology Observation of ΦCJ25

The bacteriophage ΦCJ25 purified in Example 1 was diluted in 0.01% gelatin solution, and then fixed with a 2.5% glutaraldehyde solution. The resulting bacteriophage was added dropwise to a carbon-coated mica plate (ca. 2.5 mm×2.5 mm), acclimated for 10 minutes, and then washed with distilled water.

Subsequently, the carbon film was mounted on a copper grid, and stained with 4% uranyl acetate for 60 seconds, dried, and examined under a transmission electron microscope (JEM-1011, 80 kV, magnification of ×200,000) (FIG. 1).

FIG. 1 is a transmission electron microscope image of bacteriophage ΦCJ25, in which the bacteriophage ΦCJ25 had morphological characteristics of an icosahedral capsid having a size of about 83 nm with a contractile tail, indicating that the bacteriophage belongs to morphotype A1 Myoviridae.

<Example 3>

Total Genomic DNA Size Analysis of ΦCJ25

Genomic DNA was extracted from the bacteriophage ΦCJ25 purified in Example 1.

Specifically, to a cultured solution of the purified bacteriophage ΦCJ25, 20 mM ethylenediaminetetraacetic acid (EDTA), 50 μg/ml protease K and 0.5% (w/v) sodium dodecyl sulfate (SDS) were added and left at 50° C. for one hour, to which an equal amount of phenol (pH 8.0) was added with stirring, followed by centrifugation at room temperature and 12,000 rpm for 10 minutes, thereby obtaining a supernatant.

The supernatant was mixed with an equal amount of PC (phenol: chloroform =1:1), followed by centrifugation at room temperature and 12,000 rpm for 10 minutes, thereby obtaining a supernatant. The supernatant was mixed with an equal amount of chloroform, followed by centrifugation at room temperature and 12,000 rpm for 10 minutes, thereby obtaining a supernatant. The supernatant was mixed with 10% (v/v) of 3M sodium acetate based on the total volume, followed by the addition of 2 volumes of cold 95% ethanol, mixing, and standing at −20° C. for 1 hour.

Subsequently, the resulting substance was centrifuged at 0° C. and 12,000 rpm for 10 minutes, from which a supernatant was removed to obtain a precipitate, which was dissolved in 50 μl of TE buffered solution (Tris-EDTA, pH 8.0). The extracted DNA was diluted 10 fold, and then concentration of DNA was determined by measuring absorbance at $OD_{260}$.

Figure 2:
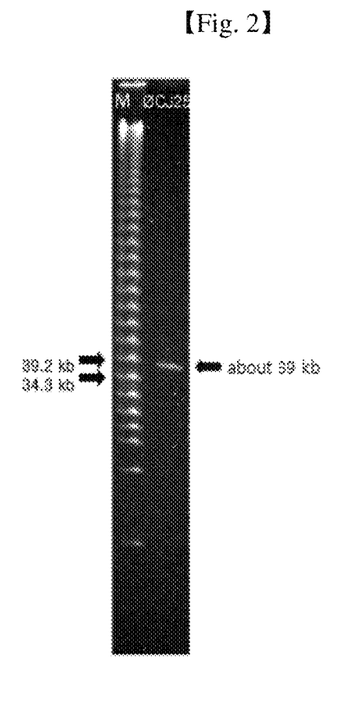
FIG. 2 shows results of pulsed field gel electrophoresis (PFGE) of a novel bacteriophage ΦCJ25.

Next, 1 μg of DNA was loaded on a 1% PFGE (pulsed field gel electrophoresis) agarose gel, and developed using BIORAD PFGE SYSTEM NO.7 PROGRAM (size ranging from 25 kb to 100 kb; switch time ramp 0.4 seconds to 2.0 seconds, linear shape; forward voltage, 180 V; reverse voltage, 120 V) at room temperature for 20 hours (FIG. 2).

FIG. 2 is an electrophoresis gel photograph of genomic DNA of the bacteriophage ΦCJ25, and it could be seen that the genomic DNA size of the bacteriophage ΦCJ25 was about 39 kbp.

<Example 4>

Protein Pattern Analysis of ΦCJ25

Figure 3:
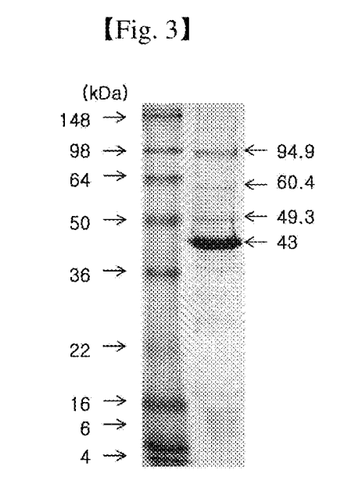
FIG. 3 shows results of sodium dodecyl sulfate polyacrylamide gel electrophoresis (SDS-PAGE) of a novel bacteriophage ΦCJ25.

15 μl of purified ΦCJ25 solution ($10^{11}$ pfu/ml titer) was mixed with 3 μl of 5×SDS sample solution, and then boiled for 5 minutes to perform 12% SDS-PAGE (FIG. 3).

FIG. 3 is an electrophoresis photograph of SDS-PAGE results performed on the bacteriophage ΦCJ25, and it could be seen that main proteins had a size of about 43 kDa, about 49.3 kDa, about 60.4 kDa and about 94.9 kDa.

<Example 5>

Analysis of Genetic Properties of ΦCJ25

In order to determine genetic properties of the bacteriophage ΦCJ25 purified in Example 1, DNA of the bacteriophage ΦCJ25 was analyzed using an FLX Titanium Sequencer (Roche) as a gene analyzer. Genes were recombined using GS and de novo assembler software (Roche) by Macrogen Inc. Open reading frame was identified using GeneMark.hmm, Glimmer v3.02 and FGENESB software. Open reading frame was annotated using BLASTP and InterProScan program.

Nucleotide sequence of the bacteriophage ΦCJ25 showed similarity to nucleotide sequence of previously reported bacteriophages (*Enterobacteria* phage EcoDS1), but it could be seen that there were no bacteriophages in which all fragments 100% coincide. Accordingly, it could be seen that the bacteriophage was a novel isolated bacteriophage.

The following Table 1 shows comparison results between nucleotide sequence of the bacteriophage ΦCJ25 and decoded nucleotide sequence of the prior reported bacteriophage in the art.

TABLE 1

| Query | | | | Subject | | Identities | |
|---|---|---|---|---|---|---|---|
| Name | Length | Start | End | Description | E-Value | Match/Total | Pct. (%) |
| SEQ ID NO: 1 | 39618 | 1 | 9030 | Enterobacteria phage EcoDS1, complete genome | 0 | 8653/9041 | 95 |

DNA of the prepared bacteriophage ΦCJ25 was analyzed using a DNA sequencer and the analyzed total nucleotide sequence is set forth in SEQ ID NO: 1.

<Example 6> pH Stability of ΦCJ25

In order to identify whether the bacteriophage ΦCJ25 can maintain stability at low pH like stomach conditions, stability of the bacteriophage ΦCJ25 was examined at various pH (pH 2.5, 3.0, 3.5, 4.0, 5.5, 6.5, 7.0, 8.0, 9.0, 10.0 and 11.0).

For the experiment, various pH solutions (sodium acetate buffer solutions (pH 4.0, pH 4.5, pH 5.0, pH 5.5), sodium citrate buffer solutions (pH 2.5, pH 3.0 and pH 3.5), sodium phosphate buffer solutions (pH 6.5 and pH 7.0), and Tris-HCl solutions (pH 8.0, pH 9.0, pH 10.0 and pH 11.0) were prepared at a concentration of 0.2M.

180 μl of each pH solution was mixed with 20 μl of a bacteriophage solution with $1.0 \times 10^{10}$ PFU/ml titer to allow each pH solution to have a concentration of 1M, and then the resulting solution was left at room temperature for 2 hours. For a control group, 20 μl of a bacteriophage solution with $1.0 \times 10^{10}$ PFU/ml titer was mixed with 180 μl of SM solution by the same method, and the resulting solution was left at room temperature for 2 hours. Thereafter, the solutions were serially diluted, and 10 μl of each of solutions in each dilution step was cultured by the soft agar overlay method at 30° C. for 18 hours to determine bacteriophage titer based on whether the bacteriophage was lysed (FIG. 4).

Figure 4:
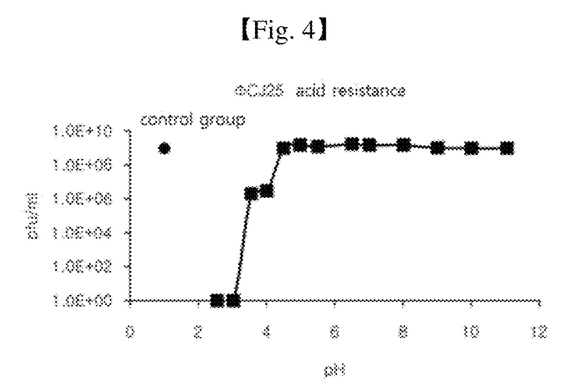
FIG. 4 is a graph depicting results of acid resistance experiment of a novel bacteriophage ΦCJ25.

FIG. 4 shows experimental results of acid resistance of the bacteriophage ΦCJ25. In FIG. 4, it could be seen that the bacteriophage ΦCJ25 did not lose its activity and maintained stability from pH 3.5 to pH 11.0, as compared with the control group.

<Example 7>

Heat Stability of Bacteriophage ΦCJ25

If bacteriophages are formulated into additives for feeds among dosage forms of bacteriophages, heat can be generated during formulation procedures, and thus, the following experiment was performed in order to determine heat stability of bacteriophages.

Specifically, 100 μl of bacteriophage ΦCJ25 solution with $1.25 \times 10^{10}$ PFU/ml was left at 37° C., 45° C., 53° C. and 60° C. for 10 minutes, 30 minutes, 60 minutes and 120 minutes, respectively. Thereafter, the resulting experimental culture solution was serially diluted, 10 μl of each of solutions in each dilution step was cultured by the soft agar overlay method at 30° C. for 18 hours to determine bacteriophage titer based on whether the bacteriophage was lysed (FIG. 5).

FIG. 5 shows experimental results of heat resistance of bacteriophage ΦCJ25. As shown in FIG. 5, it could be seen that bacteriophage ΦCJ25 did not show activity loss at 53° C. for up to 120 minutes, and showed activity decline of about 1 log or less at 60° C. for up to 120 minutes.

<Example 8>

Drying Stability of Bacteriophage ΦCJ25

If bacteriophages are formulated into additives for feeds among dosage forms of bacteriophages, bacteriophages can be dried during formulation procedures, and thus, the following experiment was performed in order to determine stability of bacteriophages against drying conditions.

Based on the results from heat resistance experiment, drying experiment was performed using a SpeedVac concentrator. 200 μl of bacteriophage ΦCJ25 solution with $1.2 \times 10^{10}$ PFU/ml was dried at 60° C. under vacuum for 2 hours, and the resulting pellets were introduced to 200 μl of SM solution, followed by completely re-suspending at 4° C. for one day, thereby measuring titers (FIG. 6).

FIG. 6 shows experimental results of drying resistance of bacteriophage ΦCJ25. As shown in FIG. 6, it could be seen that after drying, as compared with initial titers and relative stability, bacteriophage ΦCJ25 showed activity loss of about 1 log or less when dried at 60° C. for 2 hours.

<Example 9>

Examination of Infection Range of Bacteriophage ΦCJ25 on a Wild-Type Isolated Strain, Avian Pathogenic *Escherichia coli*

Lytic activity of bacteriophage ΦCJ25 was tested for 46 strains of the wild-type avian pathogenic *Escherichia coli* isolated by College of Veterinary Medicine, Konkuk University (KU), 10 strains of avian pathogenic *Escherichia coli* isolated by Korea Animal and Plant Quarantine Agency (KAPQA), 7 strains of avian pathogenic *Escherichia coli* isolated by College of Veterinary Medicine, Chonbuk National University (CNU), and 26 strains of disease-diagnosed avian pathogenic *Escherichia coli* isolated by Komipharm farm (KF) in addition to avian pathogenic *Escherichia coli* (E09-19) used in the present experiment.

Specifically, 150 μl of a shaking culture solution of each strain (OD$_{600}$=2) was mixed, and 10 μl of bacteriophage ΦCJ25 solution with $10^9$ pfu/ml titer was dropped thereto and cultured by the soft agar overlay method at 30° C. for 18 hours, and then plaque formation was examined (Table 2).

The results are shown in Table 2.

TABLE 2

| No. | KU strains | Serotyping | ΦCJ25 |
|---|---|---|---|
| 1 | E09-1 | | 0 |
| 2 | E09-2 | | 0 |
| 3 | E09-3 | | 0 |
| 4 | E09-4 | | 0 |
| 5 | E09-5 | | 0 |
| 6 | E09-6 | O-78 | 0 |
| 7 | E09-7 | | 0 |
| 8 | E09-8 | O-78 | 0 |
| 9 | E09-9 | O-78 | 0 |
| 10 | E09-10 | | 0 |
| 11 | E09-11 | O-78 | 0 |
| 12 | E09-12 | O-125 | 0 |
| 13 | E09-13 | | 0 |
| 14 | E09-14 | | 0 |
| 15 | E09-15 | | 0 |
| 16 | E09-16 | | 0 |
| 17 | E09-17 | | 0 |
| 18 | E09-18 | | |
| 19 | E09-19 | | 0 |
| 20 | E09-20 | | 0 |
| 21 | E09-21 | | 0 |
| 22 | E09-22 | | 0 |
| 23 | E09-23 | | 0 |
| 24 | E09-24 | | 0 |
| 25 | E09-25 | | 0 |
| 26 | E09-26 | | 0 |
| 27 | E09-27 | | 0 |
| 28 | E09-28 | | 0 |
| 29 | E09-29 | | 0 |
| 30 | E09-30 | | 0 |
| 31 | E09-31 | | 0 |
| 32 | E09-32 | | 0 |
| 33 | E09-33 | | 0 |
| 34 | E09-34 | | 0 |
| 35 | E09-35(297) | O-78 | |
| 36 | E09-36(343) | | 0 |
| 37 | E09-37(343) | | 0 |
| 38 | E09-38(343) | | 0 |
| 39 | E09-39(353) | | 0 |
| 40 | E09-40(353) | | 0 |
| 41 | E09-41(376) | | 0 |
| 42 | E09-42(376) | | 0 |
| 43 | E102 | O-1 | 0 |
| 44 | E103 | O-78 | 0 |
| 45 | E104 | O-78 | 0 |
| 46 | E105 | O-78 | |
| 47 | E106 | | |

| No. | KAPQA strains | Serotyping | ΦCJ25 |
|---|---|---|---|
| 48 | O6Q-035 | O-78 | 0 |
| 49 | O6D-044 | O-78 | |
| 50 | O6Q-140 | O-78 | 0 |
| 51 | O7D-001 | O-78 | 0 |
| 52 | O7D-022 | O-78 | 0 |
| 53 | O7Q-039 | O-78 | 0 |
| 54 | KWU-02 | O-78 | 0 |
| 55 | KWU-32 | O-78 | 0 |
| 56 | KWU-33 | O-78 | |
| 57 | KWU-43 | O-78 | 0 |

| No. | CNU Strains | Serotyping | ΦCJ25 |
|---|---|---|---|
| 58 | A12-MRA-076-① | | 0 |
| 59 | A10-LSf-005 | | |
| 60 | A11-LSF-043 | | |
| 61 | A12-MRA-076-② | | |
| 62 | D12-JW-058 | | 0 |
| 63 | A12-LSF-083 | O-78 | |
| 64 | A12-MRA-076-③ | | 0 |

| No. | KF Strains | Serotyping | ΦCJ25 |
|---|---|---|---|
| 65 | 12-001-3 | | 0 |
| 66 | 12-053 | | 0 |
| 67 | 12-055 | | 0 |
| 68 | 12-086-1 | O-78 | 0 |
| 69 | 12-086-2 | O-78 | 0 |
| 70 | 12-096-3 | | 0 |
| 71 | 12-175 | | 0 |
| 72 | 12-187 | O-78 | 0 |
| 73 | 12-211-5 | | 0 |
| 74 | 12-220-4 | | 0 |
| 75 | 12-220-6 | | 0 |
| 76 | 12-248 | | 0 |
| 77 | 12-261-1 | | 0 |
| 78 | 12-266 | | 0 |
| 79 | 12-274-1 | | 0 |
| 80 | 12-275-2 | O-78 | 0 |
| 81 | 12-286-2 | | 0 |
| 82 | 12-300 | O-78 | |
| 83 | 12-303-2 | O-78 | 0 |
| 84 | 12-304-3 | | 0 |
| 85 | 12-299-1 | O-78 | 0 |
| 86 | 12-299-2 | O-78 | 0 |
| 87 | 12-299-3 | O-78 | 0 |
| 88 | 12-324 | O-78 | 0 |
| 89 | 12-338-1 | O-78 | |
| 90 | 12-338-4 | O-78 | |

As shown in table 2, the bacteriophage ΦCJ25 exhibits infection ability to avian pathogenic *Escherichia coli* (including O-1, O-78, O-125 serotypes), which is a major causative bacteria of avian colibacillosis in general poultry farms.

Meanwhile, it is known that O-78 serotype is generally the most dominant strain among avian pathogenic *Escherichia coli* isolated from poultry farms.

The invention claimed is:

1. A method for preventing an infectious disease caused by avian pathogenic *Escherichia coli*, the method comprising:
   administering bacteriophage ΦCJ25 deposited as accession number KCCM11463P to birds.

2. The method for preventing an infectious disease caused by avian pathogenic *Escherichia coli* according to claim 1, wherein the infectious disease is avian colibacillosis.

3. A method for preventing an infectious disease caused by avian pathogenic *Escherichia coli*, the method comprising:
   administering a composition comprising bacteriophage ΦCJ25 deposited as accession number KCCM11463P to birds.

4. A method of preparing an additive composition, the method comprising:
   providing bacteriophage ΦCJ25 deposited as accession number KCCM11463P; and
   mixing the bacteriophage with at least one additional material to provide the additive composition.

5. The method of claim 4, wherein the bacteriophage is in an amount of 0.05 wt % to 10 wt % based on the weight of the additive composition.

6. A method of preparing a feed composition, the method comprising:
   preparing the additive composition according to the method of claim 4; and
   mixing the additive composition with an avian feed to provide the feed composition.

7. A method of feeding, the method comprising:
preparing the feed composition according to the method of claim 6; and
providing the feed composition to birds.

8. A method of preparing drinking water composition, the method comprising:
preparing the additive composition according to the method of claim 4; and
mixing the additive composition with drinking water to provide the drinking water composition.

9. A method of providing drinking water to birds, the method comprising:
preparing the drinking water composition according to the method of claim 8; and
providing the drinking water composition to birds.

* * * * *